United States Patent [19]

Payne et al.

[11] 4,188,376

[45] Feb. 12, 1980

[54] STABLE LIQUID COMPOSITIONS CONTAINING SALTS OF 1,2-BENZISOTHIAZOLIN-3-ONE

[75] Inventors: David T. Payne; Boris P. Brand, both of Manchester, England

[73] Assignee: Imperial Chemical Industries Limited, Great Britain

[21] Appl. No.: 942,811

[22] Filed: Sep. 15, 1978

[30] Foreign Application Priority Data

Sep. 30, 1977 [GB] United Kingdom ............... 40776/77

[51] Int. Cl.$^2$ ..................... A61K 31/00; A01N 9/12; A01N 9/20
[52] U.S. Cl. ..................................... 424/173; 424/270
[58] Field of Search ................................ 424/270, 173

[56] References Cited

FOREIGN PATENT DOCUMENTS 1191253 5/1970 United Kingdom .
1330531 9/1973 United Kingdom .

OTHER PUBLICATIONS

Kirk–Othmer, Encyclopedia of Chemical Technology 2nd Ed., vol. 10, 1966, pp. 646–659.

*Primary Examiner*—Leonard Schenkman
*Attorney, Agent, or Firm*—Cushman, Darby & Cushman

[57] ABSTRACT

A composition of matter comprising a solution containing from 5 to 50% by weight of an alkali metal salt of crude 1,2-benzisothiazolin-3-one in a hydroxylic organic solvent selected from at least one of dipropylene glycol, tripropylene glycol, polypropylene glycols, polyethylene glycols, lower alkyl carbitols, methanol, ethanol and mixtures of at least one of these solvents and water. Biocidal compositions suitable for indirect food contact applications and in-can preservation of water-based paints in which they are non-yellowing.

7 Claims, No Drawings

STABLE LIQUID COMPOSITIONS CONTAINING SALTS OF 1,2-BENZISOTHIAZOLIN-3-ONE

This invention relates to new compositions of matter and more particularly to stable liquid compositions containing 1,2-benzisothiazolin-3-one.

1,2-Benzisothiazolin-3-one (subsequently referred to as BIT) is known to be a very effective biocide, particularly for the protection of aqueous media against infection by micro-organisms.

By the only practicable method of manufacture, BIT is obtained from diphenyldisulphide-2,2′-dicarboxylic acid by chlorination to give the so-called thiosalicyclic acid dichloride, 1,2-$C_6H_4$(SCl)COCl. This intermediate on treatment with ammonia gives the ammonium salt of BIT from which the free compound is readily isolated.

When prepared in this way the BIT contains as the main impurity some 2,2′-bis(aminocarbonyl)diphenyldisulfphide, but this is not disadvantageous since the impurity also possesses biocidal activity. This crude BIT is entirely satisfactory for the purpose indicated above, and has been used in the form of an aqueous dispersion. However, such aqueous dispersions suffer from the disadvantage that they tend to settle out on standing and also tend to block the pumps which are used for metering controlled amounts of the dispersion into the medium being treated.

In order to overcome these disadvantages liquid formulations of crude BIT have been developed which are solutions of the product in an amine or mixture of amines, usually together with some water. These formulations are described in our United Kingdom patent specification Nos. 1,191,253 and 1,330,531. The solutions described in the first of these specifications are storage stable at temperatures down to 0° C. or slightly below, and the solutions which are described in specification No. 1,330,531 are stable at temperatures down to −10° C. By "stable" is meant that the solutions do not deposit any solid matter on prolonged standing, and do not crystallise or solidify on prolonged exposure to temperatures as low as −10° C. This latter property is important in the event that the solutions may be stored outside in winter. Should the solutions freeze as a result of exposure to even lower temperatures, the solutions should revert on thawing to the unfrozen state without any change in properties, and stability to repeated freezethaw cycles is a further desirable feature.

However, for certain applications, these amine solutions of crude BIT may not be acceptable. Thus amines are disliked in general for indirect food contact applications, for example, for use in water-based adhesives which may be employed in the food packaging industry, because amine solvents are volatile and tend to have an unpleasant odour. Furthermore, the amine solutions of crude BIT may not be suitable for use as biocides in the in-can preservation of certain water-based latices because the amine solvents may cause yellowing of the latex. It therefore became necessary to develop solutions of crude BIT which are free from the disadvantages attending the amine solutions.

BIT is known to form salts with alkali metals and these salts are water-soluble. Solutions of crude BIT in propylene glycol or diethylene glycol can also be prepared and added to water to give solutions, but stable solutions of commercially acceptable strength cannot be obtained using any of the above methods. In addition to storage stability, solutions need to have a BIT content of not less than 5% and preferably not less than about 20% by weight, and to be sufficiently mobile to pour easily, even at low temperatures, to be of commercial interest.

Solutions of alkali metal salts of crude BIT in propylene glycol, which solutions also contain some water, can be prepared having an acceptable strength and viscosity, but the stability of these solutions is unsatisfactory. These propylene glycol solutions are metastable and on storage, particularly at 0° C. or below, deposit crystalline material. The crystal form of these deposits varies according to the propylene glycol and water content of the solution. Two different types of crystal have been isolated and are believed to be a hydrate and a propylene glycol adduct (propylene glycolate) respectively of the sodium salt of BIT (subsequently referred to as Na BIT hydrate and Na BIT propylene glycolate) but the correctness or otherwise of this belief is without prejudice to the invention to be described subsequently.

It has now been found that liquid formulations of crude BIT of improved storage stability can be obtained using certain hydroxylic organic solvents.

According to the present invention there is provided a composition of matter comprising a solution containing from 5 to 50% by weight of an alkali metal salt of crude 1,2-benzisothiazolin-3-one in a hydroxylic organic solvent selected from at least one of dipropylene glycol, tripropylene glycol, polypropylene glycols, polyethylene glycols, lower alkyl carbitols, methanol, ethanol and mixtures of at least one of these solvents and water.

The alkali metal salt of crude BIT which is used may be the lithium salt but above all the sodium salt.

By "lower alkyl" we mean an alkyl group containing from 1 to 4 carbon atoms.

The solvent which is used may be any one of the above-defined hydroxylic organic solvents alone, or a mixture of any two or more of these solvents, optionally together with water.

It will be understood that in selecting a suitable solvent or mixture of solvents consideration must be given to the viscosity of the resulting solution, and high molecular weight propylene glycols and polyethylene glycols will need to be substantially diluted with a low viscosity solvent in order to obtain an easily pourable composition. Polypropylene glycols and polyethylene glycols which are solid at normal room temperatures can be used in preparing the compositions of the present invention, provided that water and/or one or more of the hydroxylic organic solvents defined above is used as co-solvent.

Propylene glycol, although not suitable on its own as a solvent for alkali metal salts of BIT for the reasons given above, may nonetheless be used in admixture with any of the hydroxylic organic solvents defined above. Thus mixtures of propylene glycol with, for example, methanol, ethanol, methyl carbitol or ethyl carbitol may be used.

A preferred solvent is dipropylene glycol.

Less preferred are methanol and ethanol, because of the low flash point of these solvents.

Particularly good results are obtained with a solution comprising about 20% by weight of crude BIT in the form of its sodium salt, about 65% by weight of dipropylene glycol and the remainder water. Other useful compositions are obtained using mixtures of propylene glycol, dipropylene glycol and tripropylene glycol, or of propylene glycol and dipropylene glycol.

The compositions may be prepared by adding the alkali metal hydroxide to the hydroxylic solvent or mixture of solvents containing a small amount of water, heating the mixture until the alkali metal hydroxide has dissolved, and then adding the crude BIT conveniently in the form of an aqueous paste. The mixture is then stirred and heated, for example, to a temperature of approximately 50° C., until the solid has dissolved. The solution is then filtered to remove any insoluble material. Alternatively the alkali metal hydroxide may be added to the hydroxylic solvent or solvents in the form of a strong aqueous solution.

Storage stability tests were carried out by cooling solutions to 0° C., −10° C. and seeding with the appropriate crystal type(s). For propylene glycol solutions Na BIT hydrate and Na BIT propylene glycolate crystals were used. For solutions containing dipropylene glycol and propylene glycol, Na BIT hydrate, Na BIT propylene glycolate and sodium salt of BIT (Na BIT) crystals were used. Na BIT crystals were the only type of crystal found in 22.9% Na BIT dipropylene glycol solutions containing less than 60% dipropylene glycol. For solutions containing propylene glycol and another solvent such as methyl carbitol or methanol Na BIT hydrate, Na BIT propylene glycolate crystals and crystals obtained by cooling saturated solutions of Na BIT in methyl carbitol or methanol were used.

Na BIT propylene glycolate crystals can be obtained by slowly cooling a solution containing 22.9% Na BIT, 56% propylene glycol and the remainder water to −10° C. Na BIT hydrate crystals can be obtained by slowly cooling a solution containing 22.9% Na BIT, 68% propylene glycol and the remainder water to 0° C.

The solutions provided by the present invention have much superior storage stability compared with solutions based on propylene glycol as the organic solvent.

The invention is illustrated but not limited by the following Examples in which parts and percentages are by weight.

EXAMPLE 1

14.5 parts of sodium hydroxide are added to 162.5 parts of dipropylene glycol and 6.4 parts of water. The mixture is heated to 70° C. and stirred until the sodium hydroxide has dissolved. 66.6 parts of crude BIT paste (equivalent to 50 parts of dry BIT) are added to the solution and the mixture is stirred and heated at 50° C. to dissolve the paste. The solution is then filtered. It contains 22.9% of the sodium salt of BIT (≡20% BIT) and 65% dipropylene glycol, the remainder being water, and has good storage stability. The solution is stable for at least 18 weeks at 0° C. and −10° C. when seeded with crystals of Na BIT hydrate, Na BIT propylene glycolate and with crystals of Na BIT. A solution containing 22.9% of the sodium salt of BIT and 65% propylene glycol crystallises under the same conditions of seeding at 0° C. and −10° C. within 1 day.

EXAMPLE 2

The 162.5 parts of dipropylene glycol used in Example 1 are replaced by a mixture of 87.5 parts of dipropylene glycol and 75.0 parts of propylene glycol. The resulting solution contains 22.9% of the sodium salt of BIT (≡20% BIT), 35% dipropylene glycol and 30% propylene glycol, the remainder being water, and has good storage stability. The solution is stable for at least 18 weeks at 0° C. and for at least 3 weeks at −10° C. when seeded with crystals of Na BIT hydrate, Na BIT propylene glycolate and with crystals of the sodium salt of BIT.

EXAMPLE 3

The 162.5 parts of dipropylene glycol and 6.4 parts of water used in Example 1 are replaced by a mixture of 125 parts of methyl carbitol and 43.9 parts of water. The resulting solution contains 22.9% of the sodium salt of BIT (≡20% BIT) and 50% methyl carbitol, the remainder being water, and has good storage stability. The solution is stable for at least 2 weeks at 0° C. when seeded with crystals of Na BIT propylene glycolate. The solution is also stable for at least 2 weeks at 0° C. when seeded with crystals obtained by cooling a saturated solution of Na BIT in methyl carbitol.

EXAMPLE 4

The 162.5 parts of dipropylene glycol and 6.4 parts of water used in Example 1 are replaced by a mixture of 100 parts of propylene glycol, 68.75 parts of methyl carbitol and 0.15 parts of water. The resulting solution contains 22.9% of the sodium salt of BIT (≡20% BIT), 40% propylene glycol and 27.5% methyl carbitol, the remainder being water, and has good storage stability. The solution is stable for at least 16 weeks at 0° C. and −10° C. when seeded with crystals of Na BIT propylene glycolate. The solution is also stable for at least 4 weeks at 0° C. and −10° C. when seeded with crystals of Na BIT hydrate. The solution is also stable for at least 2 weeks at 0° C. when seeded with crystals obtained by cooling a saturated solution of Na BIT in methyl carbitol.

EXAMPLE 5

The 162.5 parts of dipropylene glycol and 6.4 parts of water used in Example 1 are replaced by a mixture of 75 parts of methanol, 93.75 parts of propylene glycol and 0.15 parts of water. The resulting solution contains 22.9% of the sodium salt of BIT (≡20% BIT), 30% methanol and 37.5% propylene glycol, the remainder being water, and has good storage stability. The solution is stable for at least 20 weeks at 0° C. when seeded with crystals of Na BIT propylene glycolate and is also stable for at least 2 weeks at 0° C. when seeded with crystals obtained by cooling a saturated solution of Na BIT in methanol.

EXAMPLE 6

162.5 parts of dipropylene glycol and 6.4 parts of water used in Example 1 are replaced by a mixture of 75 parts propylene glycol, 68.75 parts dipropylene glycol, 25 parts tripropylene glycol and 0.15 parts water. The resulting solution contains 22.9% of the sodium salt of BIT (≡20% BIT), 30% propylene glycol, 27.5% dipropylene glycol and 10% tripropylene glycol, the remainder being water, and has good storage stability. The solution is stable for at least 13 weeks at 0° C. and −10° C. when seeded with crystals of Na BIT hydrate, and Na BIT propylene glycolate.

EXAMPLE 7

14.5 parts of sodium hydroxide are added to 170 parts of polyethylene glycol of molecular weight 300 (Carbowax 300 ex Union Carbide) and 6.4 parts of water. The mixture is heated to 70° C. and stirred until the sodium hydroxide has dissolved. 59.1 parts of crude BIT paste (different to that used in Example 1; equivalent to 50 parts dry BIT) are added to the solution and the mixture is stirred and heated at 50° C. to dissolve the paste. The solution is then filtered. It contains 22.9% of the sodium salt of BIT (≡20% BIT) and 68% polyethylene glycol of molecular weight 300, the remainder being water, and has good storage stability. The solution is stable for at least 2 weeks at 0° C. and −10° C. when seeded with crystals of Na BIT hydrate and Na BIT propylene glycolate.

EXAMPLE 8

19.0 parts of sodium hydroxide are added to 157.5 parts of dipropylene glycol. The mixture is heated to 70° and stirred. 73.5 parts of a crude BIT paste (different to those used in previous examples and equivalent to 65.5 parts of dry BIT) are added to the mixture and the mixture is stirred and heated at 50° C. to dissolve all solids. The solution is then filtered. It contains 30.0% of the sodium salt of BIT (≡26.2% BIT) and 63% dipropylene glycol, the remainder being water, and has good storage stability. The solution is stable for at least 6 weeks at 0° C. when seeded with crystals of Na BIT hydrate, Na BIT propylene glycolate and with crystals of Na BIT.

We claim:

1. A biocidal composition for the protection of aqueous media against infection by microorganisms comprising a solution containing from 5% to 50% by weight of an alkali metal salt of 1,2-benzisothiazolin-3-one in a hydroxylic organic solvent selected from the group consisting of dipropylene glycol, tripropylene glycol, polyethylene glycol, of molecular weight 300, lower alkyl carbitols and mixtures of at least one of these solvents and a solvent selected from the group consisting of propylene glycol and water said solvent being present in an amount to prevent crystallization or solidification on prolonged exposure to temperatures as low as −10° C.

2. A composition as claimed in claim 1 wherein the alkali metal salt is the sodium salt.

3. A composition as claimed in claim 1 wherein the organic solvent is dipropylene glycol.

4. A composition as claimed in claim 1 wherein the organic solvent is a mixture of propylene glycol, dipropylene glycol and tripropylene glycol.

5. A composition as claimed in claim 1 wherein the organic solvent is a mixture of propylene glycol and dipropylene glycol.

6. A composition as claimed in claim 1 which comprises approximately 20% by weight of crude 1,2-benzisothiazolin-3-one in the form of its sodium salt, approximately 65% by weight of dipropylene glycol and the remainder water.

7. A composition as claimed in claim 1 wherein the solution contains from 20% to 50% by weight of the alkali metal salt of 1,2-benzisothiazolin-3-one.

* * * * *